US007232810B2

(12) United States Patent
DeLuca et al.

(10) Patent No.: US 7,232,810 B2
(45) Date of Patent: *Jun. 19, 2007

(54) 2-METHYLENE-19-NOR-VITAMIN D2 COMPOUNDS

(75) Inventors: Hector F. DeLuca, Deerfield, WI (US); Rafal R. Sicinski, Madison, WI (US); Sumithra Gowlugari, Fremont, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/922,114

(22) Filed: Aug. 18, 2004

(65) Prior Publication Data
US 2005/0070511 A1    Mar. 31, 2005

Related U.S. Application Data

(60) Provisional application No. 60/496,415, filed on Aug. 20, 2003.

(51) Int. Cl.
*A61K 31/59* (2006.01)
*C07C 401/00* (2006.01)

(52) U.S. Cl. .................................. 514/167; 552/653
(58) Field of Classification Search ............... 514/167; 552/653

See application file for complete search history.

(56) References Cited

U.S. PATENT DOCUMENTS

| 4,588,716 | A |   | 5/1986  | DeLuca et al. |
|-----------|---|---|---------|---------------|
| 4,666,634 | A |   | 5/1987  | Miyamoto et al. |
| 4,769,181 | A | * | 9/1988  | DeLuca et al. ............. 552/653 |
| 4,973,584 | A |   | 11/1990 | DeLuca et al. |
| 5,036,061 | A |   | 7/1991  | DeLuca et al. |
| 5,086,191 | A |   | 2/1992  | DeLuca et al. |
| 5,536,713 | A |   | 7/1996  | Deluca et al. |
| 5,843,928 | A | * | 12/1998 | Deluca et al. ............. 514/167 |
| 6,440,953 | B1 |   | 8/2002  | DeLuca et al. |
| 6,479,474 | B2 |   | 11/2002 | DeLuca et al. |
| 6,673,782 | B2 |   | 1/2004  | DeLuca et al. |
| 2004/0053813 | A1 |   | 3/2004 | DeLuca et al. |

OTHER PUBLICATIONS

Ostrem et al., "24- and 26-homo-1,25-dihydroxyvitamin $D_3$: Preferential activity in inducing differentiation of human leukemia cells HL-60 *in vitro*," *Proc. Natl. Acad. Sci. USA*, vol. 84, pp. 2610-2614 (1987).

Ostrem et al., "Induction of Monocytic Differentiation of HL-60 Cells by 1,25-Dihydroxyvitamin D Analogs," *J. Biol. Chem.*, vol. 262, No. 29, pp. 14164-14171 (1987); published by The American Society for Biochemistry and Molecular Biology, Inc.

Perlman et al., "$1\alpha$,25-Dihydroxy-19-Nor-Vitamin $D_3$, A Novel Vitamin D-Related Compound with Potential Therapeutic Activity," *Tetrahedron Lett.*, vol. 31, No. 13, pp. 1823-1824 (1990); published by Pergamon Press, Great Britain.

Perlman et al., "Novel Synthesis of 19-Nor-Vitamin D Compounds," *Tetrahedron Lett.*, vol. 32, No. 52, 7663-7666 (1991); published by Pergamon Press, Great Britain.

Okano et al., "Regulatory Activities of $2\beta$-(3-Hydroxypropoxy)-$1\alpha$, 25-Dihydroxy-Vitamin $D_3$, a novel Synthetic Vitamin $D_3$ Derivative, on Calcium Metabolism," *Biochem. Biophys. Res. Commun.*, vol. 163, No. 3, 1444-1449 (1989); published by Academic Press, Inc.

(Continued)

*Primary Examiner*—Sabiha N. Qazi
(74) *Attorney, Agent, or Firm*—Andrus, Sceales, Starke & Sawall, LLP

(57) ABSTRACT

2-Methylene-19-nor-24(S) and 24(R) derivatives of $1\alpha$,25-dihydroxyvitamin $D_2$ are disclosed. These compounds are characterized by minimal bone calcium mobilization activity and relatively high intestinal calcium transport activity. This results in novel therapeutic agents for the treatment of diseases such as renal osteodystrophy, autoimmune diseases, and osteoporosis. These compounds also exhibit pronounced activity in arresting the proliferation of undifferentiated cells and inducing their differentiation to the monocyte thus evidencing use as anticancer agents and for use treating skin diseases such as psoriasis

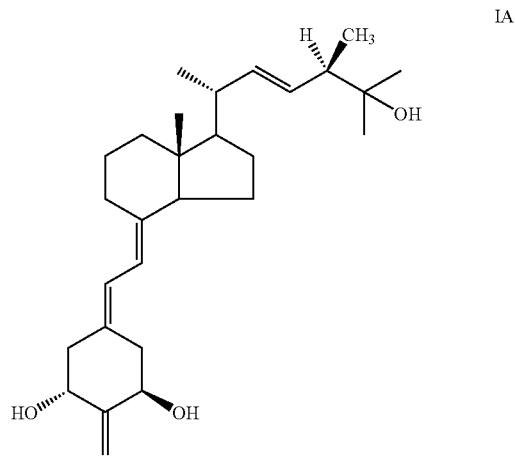

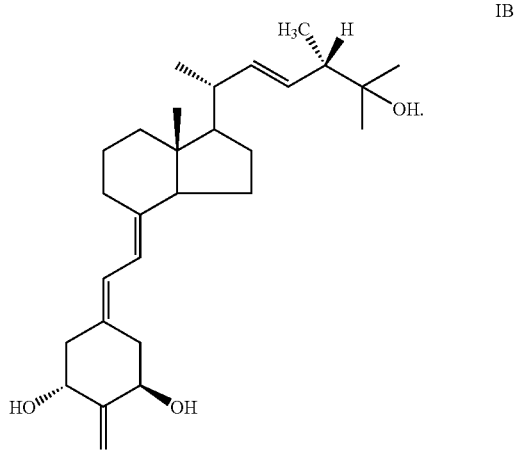

32 Claims, 4 Drawing Sheets

OTHER PUBLICATIONS

Miyamoto et al., "Synthetic Studies of Vitamin D Analogues. XIV. Synthesis and Calcium Regulating Activity of Vitamin $D_3$ Analogues Bearing a Hydroxyalkoxy Group at the 2β-Position," *Chem. Pharm. Bull.*, vol. 41, No. 6, pp. 1111-1113 (1993); published by Pharmaceutical Society of Japan.

Nishii et al., "The Development of Vitamin $D_3$ Analogues for the Treatment of Osteoporosis," *Osteoporosis Int. Suppl.*, vol. 1, 190-193 (1993); published by European Foundation for Osteoporosis.

Posner et al., Stereocontrolled Total Synthesis of Calcitriol Derivatives: 1,25-Dihydryxy-2(4'-hydroxybutyl) vitamin $D_3$ Analogs of an osteoporosis Drug, *J. Org. Chem.*, vol. 59, 7855-7861 (1994); published by American Chemical Society.

Posner et al., "2-Fluoroalkyl A-Ring Analogs of 1,25-Dihydroxyvitamin $D_3$ Stereocontrolled Total Synthesis via Intramolecular and Intermolecular Diels—Alder Cycloadditions. Preliminary Biological Testing," *J. Org. Chem.*, vol. 60, 4617-4628 (1995); published by American Chemical Society.

Lythgoe et al., "Calciferol and its Relatives. Part 22. A direct total Synthesis of Vitamin $D_2$ and Vitamin $D_3$, " *J. Chem. Soc. Perkin Trans. I*, 590-595 (1978).

Lythgoe, "Synthetic Approaches to Vitamin D and its Relatives," *Chem. Soc. Rev.*, vol. 9, 449-475 (1983).

Toh et al., "Studies on a Convergent Route to Side-Chain Analogues of Vitamin D: 25-Hydroxy-23-oxavitamin $D_3$," *J. Org. Chem.*, vol. 48, 1414-1417 (1983); published by American Chemical Society.

Baggiolini et al., "Stereocontrolled Total Synthesis of 1α,25-Dihydroxyergocalciferol," *J. Org. Chem.*, vol. 51, 3098-3108 (1986); published by American Chemical Society.

Sardina et al., "Studies on the Synthesis of Side-Chain Hydroxylated Metabolites of Vitamin D. 2. Stereocontrolled Synthesis of 25-Hydroxyvitamin $D_2$" *J. Org. Chem.*, vol. 51, 1264-1269 (1986); published by American Chemical Society.

Mascareñas et al., "Studies on the Synthesis of Side-Chain Hydroxylated Metabolites of Vitamin D. 3. Synthesis of 25-Ketovitamin $D_3$ and 25-Hydroxyvitamin $D_3$," *J. Org. Chem.*, vol. 51, pp. 1269-1272 (1986).

Mincione et al., "Improved Conversion of Vitamin $D_2$ into the Windaus Ketone and its Regioselective Hydroxylation via Organoboranes at $C_{26}$," *Synth. Commun.*, vol. 19, 723-735 (1989); published by Marcel Dekker, Inc.

Peterson et al., Studies of the Ketone Obtained from the Ozonolysis of Vitamin D. Molecular Mechanics Calculations for It and Related Hydrindanones,: *J. Org. Chem.*, vol. 51, 1948-1954 (1986); published by American Chemical Society.

Sicinski et al., "New 1α,25-Dihydroxy-19-norvitamin $D_3$ Compounds of High Biological Activity: Synthesis and Biological Evaluation of 2-Hydroxymethyl, 2-Methy., and 2-Methylene Analogues," *J. Med. Chem.*, vol. 41, 4662-4674 (1998); published by American Chemical Society.

Kutner et al., "Novel Convergent Synthesis of Side-Chain-Modified Analogues of 1α,25-Dihydroxycholecalciferol and 1α,25-Dihydroxyergocalciferol," *J. Org. Chem.*, vol. 53, 3450-3457 (1988); published by American Chemical Society.

Dame et al., "Monoclonal Antibodies to the Porcine Intestinal Receptor for 1,25-Dihydroxyvitamin $D_3$: Interaction with Distinct Receptor Domains," *Biochemistry*, vol. 25, pp. 4523-4534 (1986); published American Chemical Society.

\* cited by examiner

2-METHYLENE-19-NOR-VITAMIN D2 COMPOUNDS

CROSS-REFERENCE TO RELATED APPLICATION

This application claims priority to U.S. Application No. 60/496,415, filed Aug. 20, 2003, the entire contents of which are incorporated by reference herein and for all purposes.

FIELD OF THE INVENTION

This invention relates generally to hydroxylated vitamin $D_2$ isomers such as (20R,24R)-1α,25-dihydroxy-2-methylene-19-nor-vitamin $D_2$ and (20R,24S)-1α, 25-dihydroxy-2-methylene-19-nor-vitamin $D_2$ and pharmaceutical formulations including such compounds. The invention also relates to methods of treating various disorders using such compounds and pharmaceutical formulations.

BACKGROUND OF THE INVENTION

The natural hormone, 1α,25-dihydroxyvitamin $D_3$ and its analog in the ergosterol series, i.e., 1α,25-dihydroxyvitamin $D_2$, are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins, and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

A new class of vitamin D analogs, i.e., the so called 19-nor-vitamin D compounds, are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described [Perlman et al., Tetrahedron Lett. 31, 1823 (1990); Perlman et al., Tetrahedron Lett. 32, 7663 25(1991), and DeLuca et al., U.S. Pat. No. 5,086,191].

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as anti-tumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested [Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)].

Recently, similar analogs of 1α,25-dihydroxy-19-nor-vitamin $D_3$ have also been synthesized, i.e., compounds substituted at the 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

Recently, analogs which are characterized by the transposition of the ring A exocyclic methylene group, present in the normal vitamin D skeleton, from carbon 10 (C-10) to carbon 2 (C-2), i.e., 2-methylene-19-nor-vitamin D compounds, were synthesized and tested. Molecular mechanics studies indicate that such molecular modification does not substantially change the conformation of the cyclohexanediol ring A. However, introduction of the 2-methylene group into the 19-nor-vitamin D carbon skeleton changes the character of its (1α- and 3β-) A-ring hydroxyls. They are both now in the allylic positions, similarly, as 1α-hydroxyl group (crucial for biological activity) in the molecule of the natural hormone, 1α,25-$(OH)_2D_3$. These analogs exhibit similar rates of binding to the receptor as 1α,25-dihydroxyvitamin $D_3$ and were also characterized by high cell differentiation activity. These compounds were characterized by little, if any, intestinal calcium transport activity, as compared to that of 1α,25-dihydroxyvitamin $D_3$, while exhibiting relatively high activity, as compared to that of 1α,25-dihydroxyvitamin $D_3$ in their ability to mobilize calcium from bone.

More than ten years ago, another interesting 1α,25-dihydroxyvitamin $D_2$ analog was synthesized, namely, 1α,25-dihydroxy-24-epivitamin $D_2$, which was essentially devoid of bone calcium mobilization but unexpectedly exhibited comparable binding to the receptor as 1α,25-dihydroxyvitamin $D_3$ [DeLuca et al., U.S. Pat. No. 5,036,061]. Related patents referring to 1α,25-dihydroxy-24-epivitamin $D_2$ include DeLuca et al., U.S. Pat. No. 4,769,181, DeLuca et al., U.S. Pat. No. 54,973,584, and DeLuca et al., U.S. Pat. No. 4,588,716. In a continuing effort to explore the 19-nor class of pharmacologically important vitamin D compounds, a 19-nor-vitamin D analog, characterized by the presence of methylene substituent at the carbon 2 (C-2) and 24 R in the side chain, has now been synthesized and tested.

SUMMARY OF THE INVENTION

A class of 1α-hydroxylated vitamin D compounds not known heretofore are the vitamin $D_2$ isomers in which the A-ring exocycle methylene group, typical of all vitamin D system has been transposed to the carbon 2, i.e., 19-nor-vitamin $D_2$ analogs, having a methylene group at the 2-position, and the methyl group at carbon 24 (C-24) in the side chain having the R (i.e., 24-epi) and S configurations.

The present invention is thus directed toward the 2-methylene-19-nor-24(S)- and 24(R)-derivatives of 1α,25-dihydroxyvitamin $D_2$, their biological activity, and various pharmaceutical uses for these compounds. The compounds may be used to treat various diseases or disorders and may be used to prepare medicaments for the treatments of disorders and diseases as described herein.

Structurally, the novel analogs are characterized by the general formula I shown below:

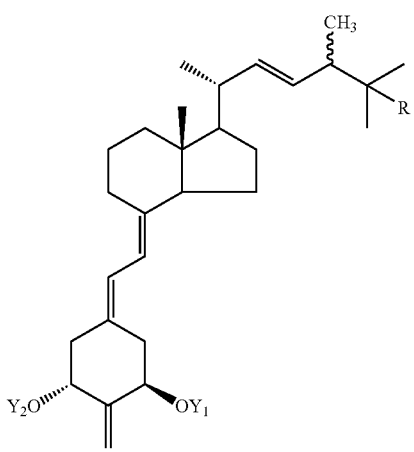

I where $Y_1$ and $Y_2$, may be the same or different, and are each selected from H or a hydroxy-protecting group, and R is selected from OH and protected hydroxy groups.

The wavy line to the methyl substituent at C-24 indicates that the methyl substituent at carbon 24 may have either the R or S configuration.

The above compounds exhibit a desired, and highly advantageous, pattern of biological activity. These compounds bind better to the vitamin D receptor than $1\alpha,25$-dihydroxyvitamin $D_3$ and are characterized by relatively high intestinal calcium transport activity, similar to that of $1\alpha,25$-dihydroxyvitamin $D_3$, but exhibit very minimal activity, as compared to $1\alpha,25$-dihydroxyvitamin $D_3$, in their ability to mobilize calcium from bone. Hence, these compounds are highly specific in their calcemic activity. Their preferential activity on gut calcium absorption allows the in vivo administration of these compounds for the treatment of metabolic bone diseases where bone loss is a major concern. Therefore, in some embodiments, these compounds or pharmaceutical formulations may be employed as therapeutic agents for the treatment of diseases or disorders where bone formation is desired, such as osteoporosis, senile osteoporosis or postmenopausal osteoporosis, as well as osteomalacia and renal osteodystrophy. In some embodiments, the treatment may be transdermal, oral, or parenteral. In some embodiments, the compounds may be present in a composition in an amount from about 0.1 µg/gm to about 100 µg/gm of the composition. In some such embodiments, the compounds are present in an amount preferably from about 0.1 µg/gm to about 50 µg/gm of the composition, and may be administered in dosages of from about 0.01 µg/day to about 100 µg/day, and in some embodiments from about 0.1 µg/day to about 50 µg/day.

The compounds of the invention are also especially suited for treatment and prophylaxis of human disorders which are characterized by an imbalance in the immune system, e.g., in autoimmune diseases, including multiple sclerosis, diabetes mellitus, hot versus graft reaction, and rejection of transplants; and additionally, for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compounds of the invention. Dosages may be the same as noted above for the metabolic bone diseases.

The above compounds are also characterized by high cell differentiation activity. Thus, these compounds also provide therapeutic agents for the treatment of psoriasis, or as anti-cancer agents, especially against leukemia, colon cancer, breast cancer and prostate cancer. The compounds may be present in a composition to treat psoriasis in an amount from about 0.01 µg/gm to about 100 µg/gm of the composition, preferably from about 0.1 µg/gm to about 50 µg/gm of the composition, and may be administered topically, transdermally, orally or parenterally in dosages of from about 0.01 µg/day to about 100 µg/day, preferably from about 0.1 µg/day to about 50 µg/day.

DETAILED DESCRIPTION OF THE INVENTION

Figure 1:
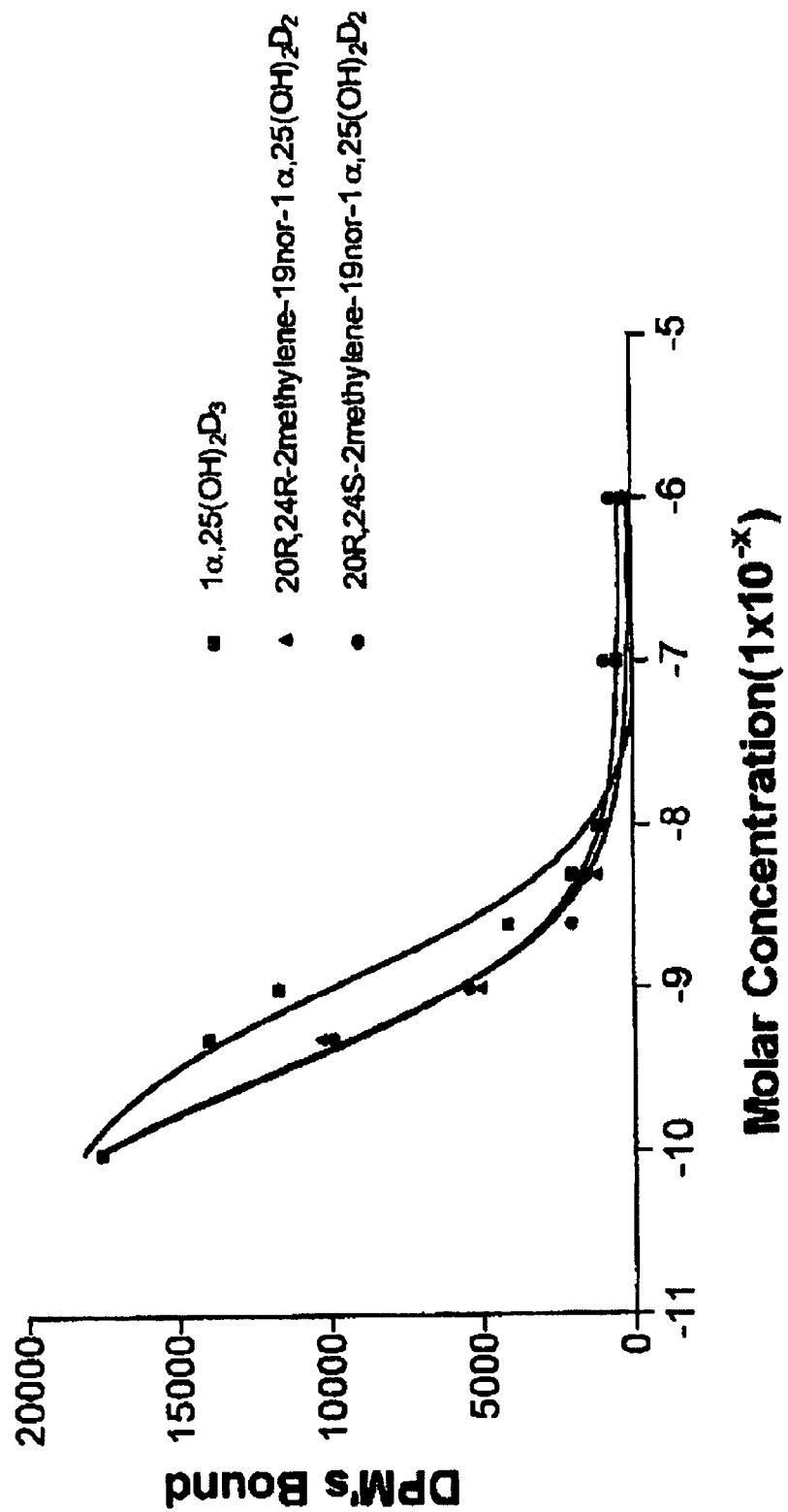
FIG. 1 is a graph illustrating the relative activity of 2-methylene-19-nor-24(S)-20(R)-1α,25-dihydroxyvitamin $D_2$, 2-methylene-19-nor-24(R)-20(R)-1α,25-dihydroxyvitamin $D_2$ and 1α,25-dihydroxyvitamin $D_3$ to compete for binding of [$^3$H]-1α,25-(OH)$_2$-$D_3$ to the vitamin D pig intestinal nuclear receptor.

The 2-methylene-19-nor-24 (S) and 24 (R) derivatives of 1α,25-dihydroxyvitamin $D_2$ were synthesized and tested. Structurally, these 19-nor analogs are characterized by the general formula I previously illustrated herein.

In some aspects, the invention provides (20R,24R)-1α, 25-dihydroxy-2-methylene-19-nor-vitamin $D_2$ having the formula IA:

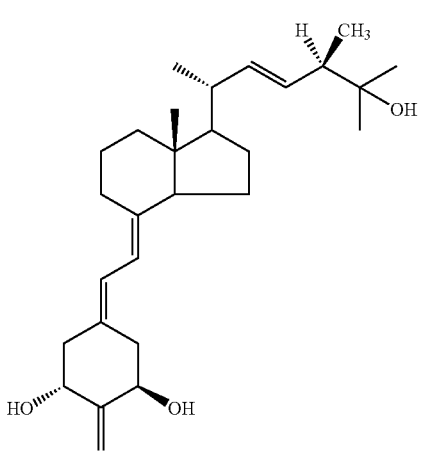

IA and (20R,24S)-1α,25-dihydroxy-2-methylene-19-nor-vitamin D$_2$ having the formula IB:

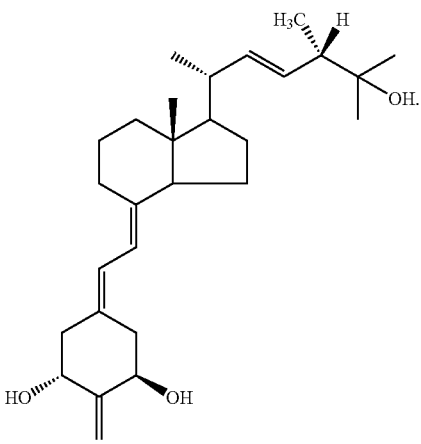

IB

As used in the description and in the claims, the term "hydroxy-protecting group" signifies any group commonly used for the temporary protection of hydroxy functions, such as, for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, Triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is herein incorporated by reference in its entirety as if fully set forth herein.

A "protected hydroxy" group is a hydroxy group derivatized or protected by any of the above groups commonly used for the temporary or permanent protection of hydroxy functions, e.g., the silyl, alkoxyalkyl, acyl or alkoxycarbonyl groups, as previously defined. The terms "hydroxyalkyl, ""deuteroalkyl," and "fluoroalkyl" refer to an alkyl radical substituted by one or more hydroxy, deuterium or fluoro groups respectively.

The preparation of 1α,25-dihydroxy-2-methylene 19-nor-vitamin D$_2$ compounds having the basic structure I can be accomplished by a common general method, i.e., the condensation of a bicyclic Windaus-Grundmann type ketone II with the allylic phosphine oxide III followed by Julia's olefination with the sulfone IV:

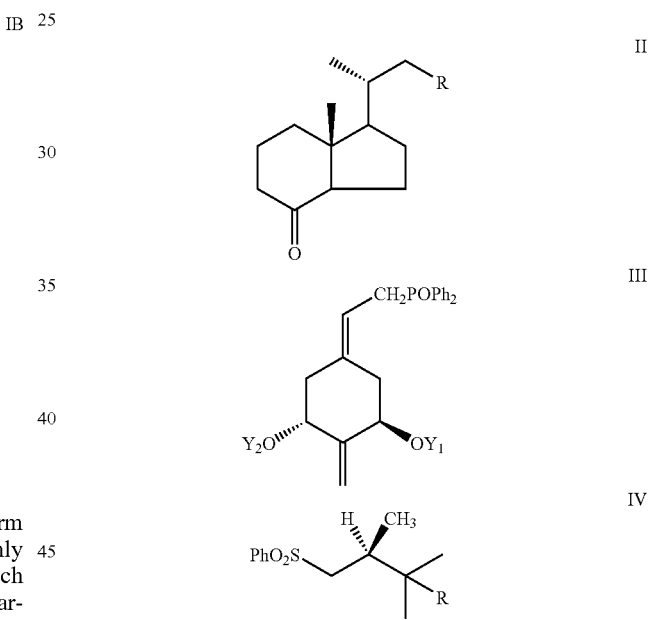

In the structures II, III and IV groups, Y$_1$ and Y$_2$ and R represent groups defined above; Y$_1$ and Y$_2$ are preferably hydroxy-protecting groups, R is either hydroxyl or protected hydroxyl, it being also understood that any functionalities in R that might be sensitive, or that interfere with the condensation reaction, be suitably protected as is well-known in the art. The process shown above represents an application of the convergent synthesis concept, which has been applied effectively for the preparation of vitamin D compounds [e.g., Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II are known, or can be prepared by known methods. Specific important examples of such known bicyclic ketones are Grundmann's ketone analogs (a and b) [Mincione et al., Synth. Commun 19, 723, 1989; Peterson et al., J. Org. Chem. 51, 1948, (1986)].

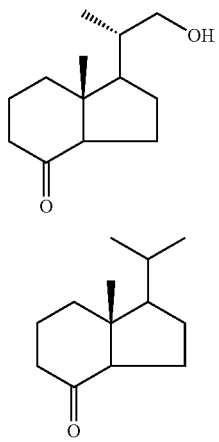

2-Methylene phosphine oxide III can be prepared according to the procedure described by Sicinski et al., J. Med. Chem., 41, 4662 (1998), DeLuca et al., U.S. Pat. No. 5,843,928.

The protected hydroxy sulfone compound IV can be prepared according to the procedure described by Kutner et al., J. Org. Chem. 53, 3450 (1988).

For the preparation of the required Grundmann's ketone analog of the general structure II, a new synthetic route has been developed starting from the diol 2, easily obtained from the commercial vitamin $D_2$ as described by Sardina et al., J. Org. Chem. 51, 1264, (1986). The overall process for the synthesis of the vitamin D analog 10 is summarized in SCHEME I. Thus, the diol 2, obtained by the ozonolysis of vitamin $D_2$, was protected as mono triethyl silyl ether 3, and the secondary hydroxyl at C-8 was oxidized with PDC to get the Grundmann's ketone 4. Wittig-Horner coupling of the conjugate base of the phosphine oxide 5, produced upon deprotonation with phenyllithium, with the protected 22-hydroxy Grundmann's ketone produced the expected protected 19-nor-pregnacalciferol 6 in a high yield. The triethylsilyl protecting group of the compound 6 was cleaved using 8:8:1 mixture of AcOH:THF:$H_2O$. The hydroxy vitamin D analog 7 (SCHEME II) was then converted into its carbonyl derivative 8 under Swern oxidation conditions using $(COCl)_2$, DMSO and TEA, which on Julia's olefination with the sulphone 9 followed by desulfonylation gave the protected analog 10. The final step involved the unmasking of the silyl ethers with tetrabutylammonium fluoride to yield 24R-1α, 25-dihydroxy-2-methylene-19-nor-vitamin $D_2$, 11. Notably, 24S-1α,25-dihydroxy-2-methylene-19-nor-vitamin $D_2$ may be synthesized using the same procedure employing the enantiomer of the sulphone shown in SCHEME II.

This invention is described by the following illustrative examples which are not meant to limit the invention in any manner. In these examples specific products identified by Arabic numerals (e.g., 1, 2, 3, etc.) refer to the specific structures so identified in the preceding description and in SCHEME I and SCHEME II.

EXAMPLE 1

Preparation of 24-R-1α,25-dihydroxy-2-methylene-19-nor-vitamin $D_2$, 11 a) Ozonolysis of Vitamin $D_2$

A solution of vitamin $D_2$ (2.00 g. 5.05 mmol) in absolute methanol (175 mL) and pyridine (1.75 mL) was placed in an ozonation vessel provided with a magnetic stirring bar. The solution was cooled to −78° C. while purging with oxygen. A stream of ozone was then passed until a deep blue color appeared (1 hour). The ozone flow was discontinued, and the reaction mixture was purged with oxygen (−78° C.) until no ozone remained in solution. $NaBH_4$ (500 mg) was added in one portion, and the resulting solution was stirred at −78° C. for 20 minutes while a gentle flow of $N_2$ was maintained. The reaction was allowed to stir at room temperature overnight. An additional quantity of $NaBH_4$ (500 mg) was added at room temperature, and the resulting solution was stirred for 30 minutes. The resulting solution was rotary evaporated to a small volume, and the residue was extracted with ether. The ethereal layers were washed with 5% HCl and $H_2O$ and then dried over $Na_2SO_4$. Filtration and concentration in vacuo afforded a residue that was flash chromatographed (25% EtOAc/75% hexane) to yield diol 2 (1.2 g, 82%): $^1$H NMR ($CDCl_3$) δ 0.958 (3H, s, 18-$CH_3$), 1.03 (2H, d, J=6.6 Hz, 21-$CH_3$), 3.38 (1H, dd, J=6.7, 10.5 Hz, 22-H), 3.64 (1H, dd, J=3.5, 10.5 Hz, 22-H), 4.09 (1H, m, 8α-H).

b) Preparation of Silyl Ether 3

De-A,B-23,24-dinor-22-(triethylsilyloxy)-cholan-8β-ol (3)

To a solution of the diol 2 (100 mg, 0.472 mmol) in anhydrous acetonitrile (250 μL) and 2,6-lutidine (138 μL, 1.17 mmol) was added triethylsilyl trifluoromethanesulfonate (118 μL, 0.518 mmol). The reaction was then stirred at room temperature under argon for 2 hours, quenched with water, and extracted with ethyl acetate. The organic layer was washed with brine solution and then dried over $Na_2SO_4$. The organic extracts were evaporated to afford the crude product, which was purified by silica gel chromatography to yield (120 mg, 80%) of silyl ether 3: $^1$H NMR ($CDCl_3$) δ 0.575 (6H, q, 3×Si$CH_2$), 0.947(9H, t, 3×Si$CH_2CH_3$), 0.958 (3H, s, 18-$CH_3$), 1.03 (2H, d, J=6.6 Hz, 21-$CH_3$), 3.24 (1H, dd, J=7.7, 9.6 Hz, 22-H), 3.59 (1H, dd, J=3.5, 9.6 Hz, 22-H), 4.08 (1H, m, 8α-H).

c) Oxidation of the 8β-Hydroxyl Group in Compound 3

De-A,B-23,24-dinor-22-[(triethylsilyl)oxy]-8-oxo-cholane (4)

Pyridinium dichromate (87.6 mg, 0.232 mmol) was added to a solution of alcohol 3 (50 mg, 0.155 mmol) and pyridinium p-toluenesulfonate (10 mg) in $CH_2Cl_2$ (2 mL). The resulting orange suspension was stirred for 3 hours at room temperature. Ether was added, and the resulting suspension was filtered through a short column of Celite. The filtrate was washed with a saturated aqueous solution of $CuSO_4$ and $H_2O$, dried over $Na_2SO_4$, and filtered. Removal of solvents under reduced pressure afforded the ketone, which was then purified by column chromatography. The compound was further purified by HPLC (250×10 mm Zorbax-Sil column, 4 mL/minute) using 90:10 mixture of hexane/ethyl acetate as eluents. Pure protected ketone 4 (38 mg, 79%) eluted at $R_v$ 17 mL: $^1$H NMR (CDCl$_3$) δ 0.582 (6H, q, 3×SiCH$_2$), 0.643 (3H, s, 18-CH$_3$), 0.952 (9H, t, 3×SiCH$_2$CH$_3$), 1.036 (3H, d, J=6.1, 21-CH$_3$), 3.29 (1H, dd, J=6.9, 9.6 Hz, one of 22-H), 3.58 (1H, dd, J=2.8, 9.6 Hz, one of 22-H).

d) Wittig-Horner Condensation of Phosphine Oxide 5 with Protected Grundmann's Ketone 4

(3'R,5'R)-3'5'-Bis[(tert-butyldimethylsilyl)oxy]-(20S)-20-[(triethylsilyl)oxy]methyl-2-methylene-19-nor-pregnacalciferol(6)

To a solution of phosphine oxide 5 (13 mg, 0.0218 mmol) in anhydrous THF (130 μL) at 0° C. was slowly added PhLi (18 μL, 0.0327 mmol) under argon with stirring. The solution turned deep orange. The mixture was cooled to −78° C. and a pre-cooled (−78° C.) solution of protected hydroxy ketone 4 (8.5 mg, 0.0262 mmol) in anhydrous THF (170 μL) was slowly added. The mixture was stirred at −78° C. for 2.5 hours and then at 0° C. for 18 hours. Ethyl acetate was added, and the organic phase was washed with brine, dried over MgSO$_4$, and evaporated. The residue was dissolved in hexane, applied on a silica Sep-Pak cartridge, and washed with hexane/ethyl acetate (99.7:0.3, 20 mL) to give 19-nor-vitamin derivative 6. The vitamin derivative was further purified by HPLC (250×10 mm Zorbax-Sil column, 4 mL/minute) using a hexane/ethyl acetate (99.9:0.1) solvent system. Pure compound 6 was eluted at R$_v$ 22 mL as a colorless oil: UV (in ethanol) λ$_{max}$ 244, 252, 262 nm; $^1$H NMR (CDCl$_3$) δ 0.026. 0.047, 0.065 and 0.079 (each 3H, each s, 4×SiCH$_3$), 0.559 (3H, s, 18-CH$_3$), 0.593(6H, q, 3×SiCH$_2$), 0.864 and 0.894 (each 9H, each s, 2×Si-t-Bu), 0.966 (9H, t, 3×SiCH$_2$CH$_3$), 1.019 (3H, d, J=6.5, 21-CH$_3$), 3.25 (1H, dd, J=7.9, 9.5 Hz, 22-H), 3.624 (1H, dd, J=3.4, 9.6, 22-H), 4.42 (2H, m, 1α-H, 3β-H), 4.92 and 4.96 (each CH$_2$), 5.84 (1H, d, J=11.2 Hz, 7-H) and 6.21 (1H, d, J=1.2 Hz, 6-H); MS m/z (relative intensity): 688 (M+, 34), 659 (M+—CH$_3$), 557 (M+—OSi(CH$_3$)$_2$t-Bu, 50).

e) Cleavage of Triethylsilyl Ether in the Vitamin Analog 6

(3'R,5'R)-3' 5'-Bis [(tert-butyldimethylsilyl)oxy]-(20S)-20-hydroxymethyl-2-methylene-19-nor-pregnacalciferol (7)

To a solution of the 19-nor-vitamin derivative 6 (1.5 mg, 0.002 mmol) in 50 μL benzene was added 200 μL of an 8:8:1 mixture of AcOH:THF:H$_2$O. The resulting mixture was stirred for 2 hours. The reaction mixture was then quenched with an aqueous solution of NaHCO$_3$ and extracted with ether. The combined ether layers were washed with brine, dried over Na$_2$SO$_4$, and the solvent evaporated affording the alcohol which was further purified by silica column chromatography with 95:5 mixture of hexane/ethyl acetate to yield (1 mg, 80%) of pure 7: $^1$H NMR (CDCl$_3$) δ 0.026, 0.047, 0.064 and 0.078 (each 3H, each s, 4×SiCH$_3$), 0.571 (3H, s, 18-CH$_3$), 0.864 and 0.895 (each 9H, each s, 2×Sit-Bu), 1.065 (3H, d, J=6.6, 21-CH$_3$), 3.401 (1H, dd, J=7.0, 10.4 Hz, 22-H), 3.65 (1H, dd, J=3.3, 15.4, 22-H), 4.42 (2H, m, 1α-H, 3β-H), 4.92 and 4.97 (each 1H, each s, =CH$_2$), 5.84 (1H, d, J=11.3 Hz, 7-H) and 6.21 (1H, d, J=11.0 Hz, 6-H); MS m/z (relative intensity) 574 (M+, 17), 559 (M+—CH$_3$, <1), 442 (M+—OSi(CH$_3$)$_2$t-Bu, 64).

f) Swern Oxidation of the Hydroxy Compound to the Carbonyl Derivative (3'R,5'R)-3'5'-Bis [(tert-butyldimethylsilyl)oxy]-(20S)-20-al-2-methylene-19-nor-pregnacalciferol (8)

A solution of 16.6 μL (0.13 mmol) of oxalyl chloride in 0.5 mL of 20 dichloromethane was added dropwise to a stirred solution of 21 μL (0.26 mmol) of DMSO in 3 mL of dichloromethane at −78° C. under argon. After the mixture was stirred for 10 minutes at −78° C., the solution of 11 mg (0.0 19 mmol) of alcohol 7 in 1 mL dichloromethane was slowly added. The mixture was stirred for 30 minutes at −78° C. and 0.1 mL of triethylamine was added. The product aldehyde 8 was extracted with ethyl acetate, washed with saturated NaCl, and dried over Na$_2$SO$_4$. Silica gel Sep-Pak filtration afforded the pure aldehyde: $^1$H NMR (CDCl$_3$) δ 0.029, 0.032, 0.041 and 0.059 (each 3H, each s, 4×SiCH$_3$), 0.574 (3H, s, 18-CH$_3$), 0.838 and 0.8792 (each 9H, each s, 2×Sit-Bu), 1.1216 (3H, d, J=6.8, 21-CH$_3$), 4.40 (2H, m, 1β-H, 3α-H), 4.92 and 4.97 (each 1H, each s, CH$_2$), 5.84 (1H, d, J=9.7 Hz, 7-H) and 6.18 (1H, d, J=12.1 Hz, 6-H); 9.57 (1H, s, 22-H).

g) Addition of Sulfone 9 to the Aldehyde 8

(1α,3β-24R)-1,3-Bis [(tert-butyldimethylsilyl)oxy]-25-(triethylsilyl)oxy-2-methylene-19-nor-vitamin D$_2$ (10)

To a solution of n-BuLi in hexanes containing 1,10-phenanthroline indicator was added 11.1 μL (0.11 mmol) of diisopropylamine with stirring under argon at −78° C. (red color). After the mixture was stirred for 20 minutes, the solution of 23.4 mg (0.11 mmol) of sulfone 9 in 0. 5 mL of anhydrous THF, was added dropwise. The mixture was stirred at −75° C. for 30 minutes, and a solution of 5 mg of aldehyde 8 in 0.5 mL of THF was added. Stirring was continued for 1.5 hours and a solution of saturated NH$_4$Cl solution was added. The reaction mixture was extracted with ethyl acetate, and the organic phase was washed with saturated NaCl. Without further purification, the product was acetylated. The compound was taken in anhydrous dichloromethane and acetic anhydride and pyridine were added at 0° C. After reaction completion, the reaction mixture was washed with a saturated CuSO$_4$ solution and extracted with dichloromethane. The product was used in the next reaction without any purification. A saturated solution of Na$_2$HPO$_4$ in methanol 0.5 mL) was added to a stirred solution of the sulfone (1.80 mg) in 0.5 mL of anhydrous THF. The mixture was stirred under argon for 30 minutes and cooled to 0° C. Fresh 5% sodium amalgam (ca 200 mg) was then added, and the mixture was stirred for 3 hours at 5° C. The mixture was diluted with 3 mL of hexane and stirring was continued for 15 minutes. The hexane layer was then decanted, and the methanol layer was washed with hexane (3×2 mL). The hexane layer was washed with ice-cold saturated NaCl and then dried over Na$_2$SO$_4$. The compound was purified on a silica Sep-Pak cartridge using 99:1 mixture of hexane/ethyl acetate providing 10: $^1$H NMR (CDCl$_3$) δ 0.007, 0.028, 0.046 and 0.061 (each 3H, each s, 4×SiCH$_3$), 0.537 (3H, s, 18-CH$_3$), 0.56(6H, q, 3×SiCH$_2$), 0.848 and 0.877 (each 9H, each s, 2×Sit-Bu), 0.938 (9H, t, 3×SiCH$_2$CH$_3$), 0.991 (3H, d, J=6.5, 21-CH$_3$), 4.40 (2H, m 1α-H, 3β-H), 4.902 and 4.949(each 1H, each s, =CH$_2$), 5.188(1H, dd, J=8.29, 15.24 Hz, 22-H), 5.275 (1H, dd, J=8.37, 15.28 Hz, 23-H), 5.817 (1H, d, J=11.1 Hz, 7-H) and 6.191 (1H, d, J=11.0 Hz, 6-H).

h) Deprotection of Silyl Ethers of the Vitamin Analog 10

(24R)-1α,25-Dihydroxy-2-methylene-19-nor-vitamin D$_2$

Protected vitamin 10 (2 mg, 0.0046 mmol) was dissolved in anhydrous THF (350 μL) and 20 tetrabutylammonium fluoride (TBAF) (7.3 μL, 0.0116 mmol) was added, and the reaction was stirred at room temperature for 2 hours under argon. The reaction was then quenched with water and extracted with ether, washed with brine, dried over Na$_2$SO$_4$, and evaporated. The residue was purified by HPLC (250×6.2 mm Zorbax-ODS reversed phase column, 2 mL/minute) using methanol/water (90:10) solvent system. Pure vitamin derivative 11 was eluted at R$_v$ 15.5 mL (960 μg, 85%): UV (in ethanol) λ$_{max}$ 243.5, 251.5, 261 nm; $^1$H NMR (CDCl$_3$) δ 0.568 (3H, s, 18-CH$_3$), 0.997 (3H, d, J=6.9 Hz, 28-CH$_3$), 1.03403H, d, J=6.6 Hz, 21-CH$_3$), 1.134 (3H, s, 26-CH$_3$), 1.178 (3H, s, 27-CH$_3$), 4.478 (2H, m, 1β-H, 3α-H), 5.09 and 5.11 (each 1H, each s, =CH$_2$),5.275 (1H, dd, J=8.66, 15.24 Hz, 22-H), 5.355 (1H, dd, J8.45, 15.23 Hz, 23-H), 5.873 (1H, d, J=11.28 Hz, 7-H) and 6.354 (1H, d, J=10.99 Hz, 6-H); MS m/z (relative intensity) 428 (M+, 100), 410 (M+—H$_2$O), 287 (M+—side 10 chain, 33).

SCHEME I

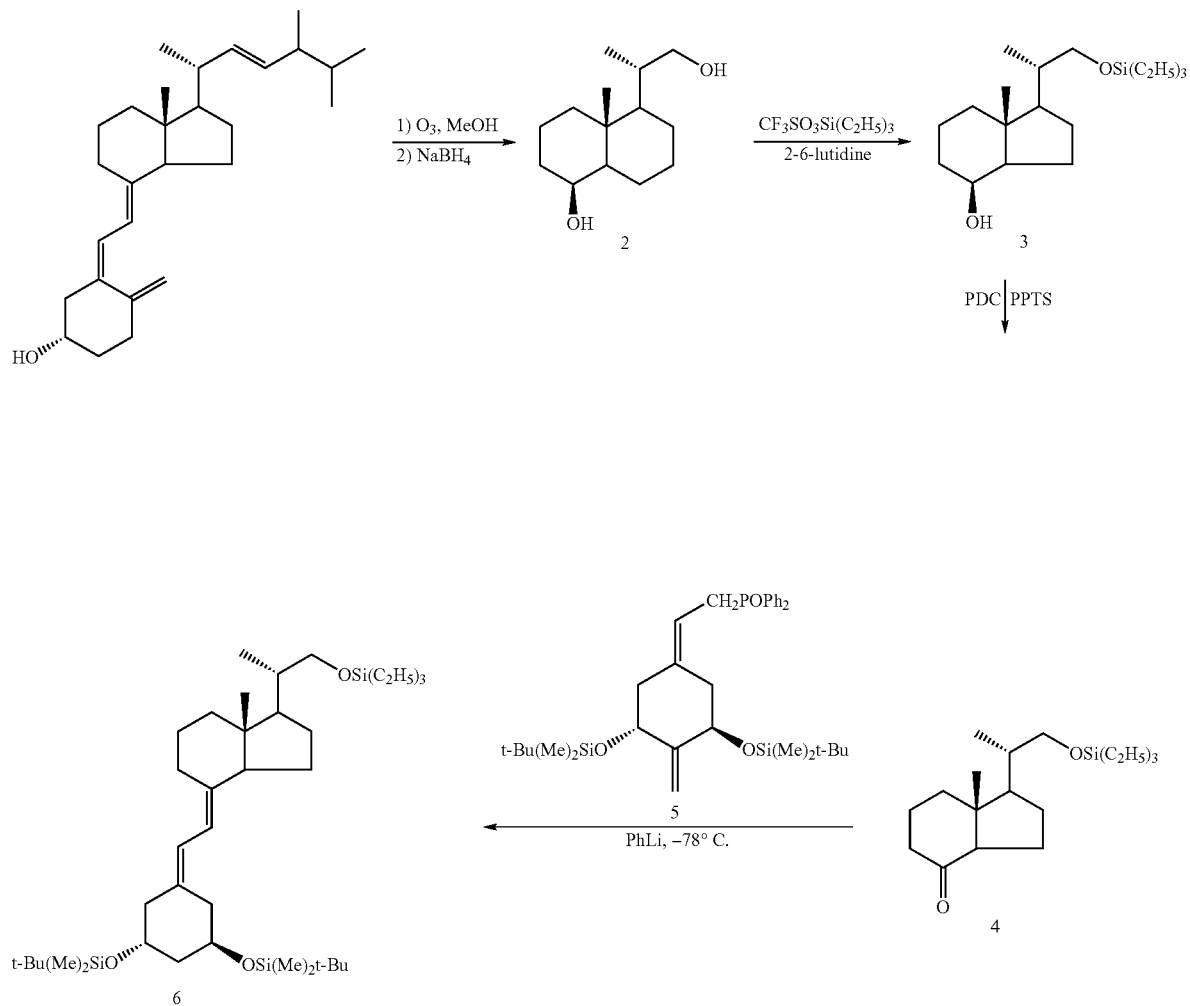

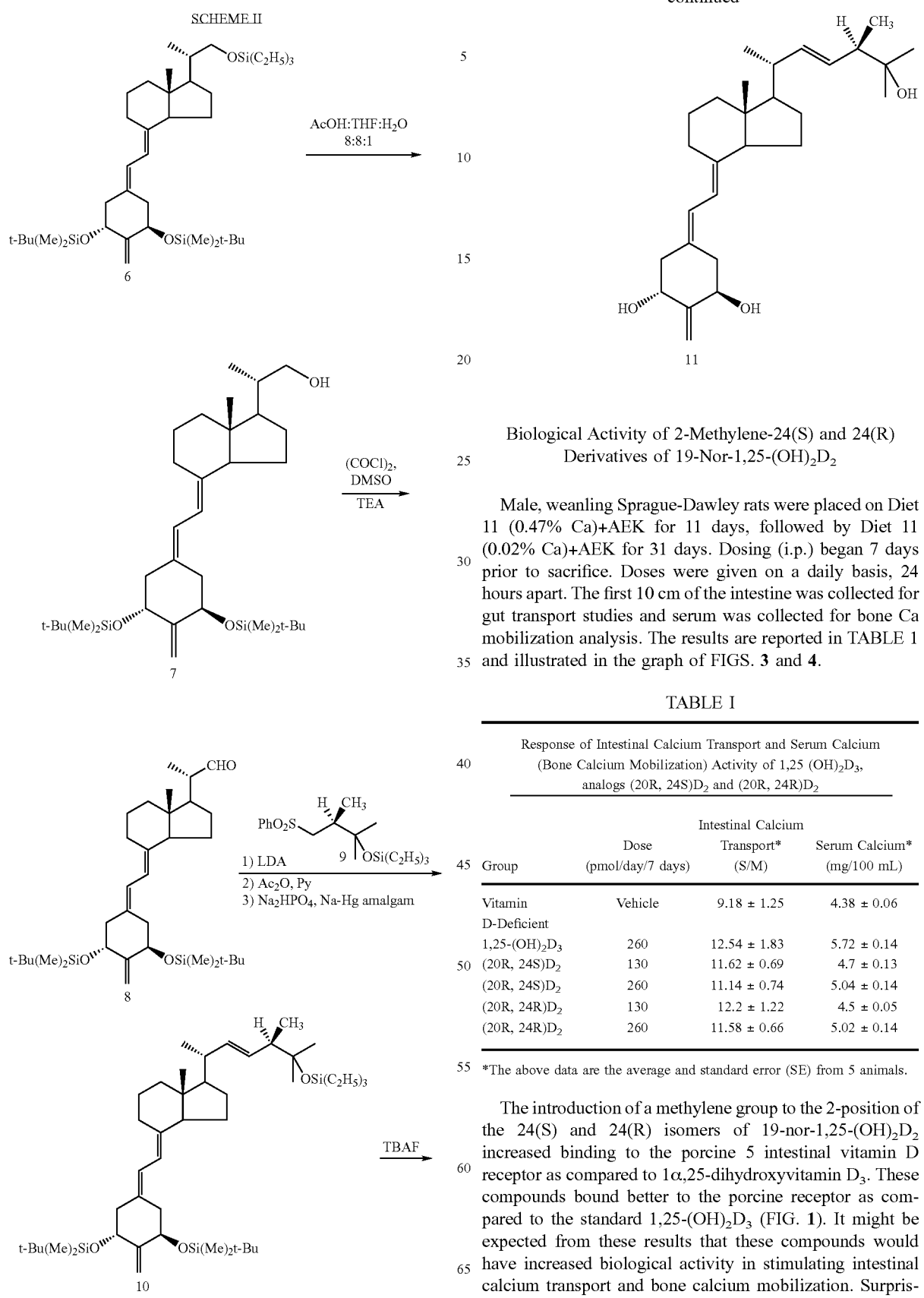

SCHEME II

Biological Activity of 2-Methylene-24(S) and 24(R) Derivatives of 19-Nor-1,25-(OH)$_2$D$_2$ Male, weanling Sprague-Dawley rats were placed on Diet 11 (0.47% Ca)+AEK for 11 days, followed by Diet 11 (0.02% Ca)+AEK for 31 days. Dosing (i.p.) began 7 days prior to sacrifice. Doses were given on a daily basis, 24 hours apart. The first 10 cm of the intestine was collected for gut transport studies and serum was collected for bone Ca mobilization analysis. The results are reported in TABLE 1 and illustrated in the graph of FIGS. 3 and 4.

TABLE I

Response of Intestinal Calcium Transport and Serum Calcium (Bone Calcium Mobilization) Activity of 1,25 (OH)$_2$D$_3$, analogs (20R, 24S)D$_2$ and (20R, 24R)D$_2$

| Group | Dose (pmol/day/7 days) | Intestinal Calcium Transport* (S/M) | Serum Calcium* (mg/100 mL) |
|---|---|---|---|
| Vitamin D-Deficient | Vehicle | 9.18 ± 1.25 | 4.38 ± 0.06 |
| 1,25-(OH)$_2$D$_3$ | 260 | 12.54 ± 1.83 | 5.72 ± 0.14 |
| (20R, 24S)D$_2$ | 130 | 11.62 ± 0.69 | 4.7 ± 0.13 |
| (20R, 24S)D$_2$ | 260 | 11.14 ± 0.74 | 5.04 ± 0.14 |
| (20R, 24R)D$_2$ | 130 | 12.2 ± 1.22 | 4.5 ± 0.05 |
| (20R, 24R)D$_2$ | 260 | 11.58 ± 0.66 | 5.02 ± 0.14 |

*The above data are the average and standard error (SE) from 5 animals.

The introduction of a methylene group to the 2-position of the 24(S) and 24(R) isomers of 19-nor-1,25-(OH)$_2$D$_2$ increased binding to the porcine 5 intestinal vitamin D receptor as compared to 1α,25-dihydroxyvitamin D$_3$. These compounds bound better to the porcine receptor as compared to the standard 1,25-(OH)$_2$D$_3$ (FIG. 1). It might be expected from these results that these compounds would have increased biological activity in stimulating intestinal calcium transport and bone calcium mobilization. Surprisingly, however, the 2-methylene and 24-epi substitutions produced highly selective analogs with their primary action on stimulating intestinal calcium transport.

Figure 2:
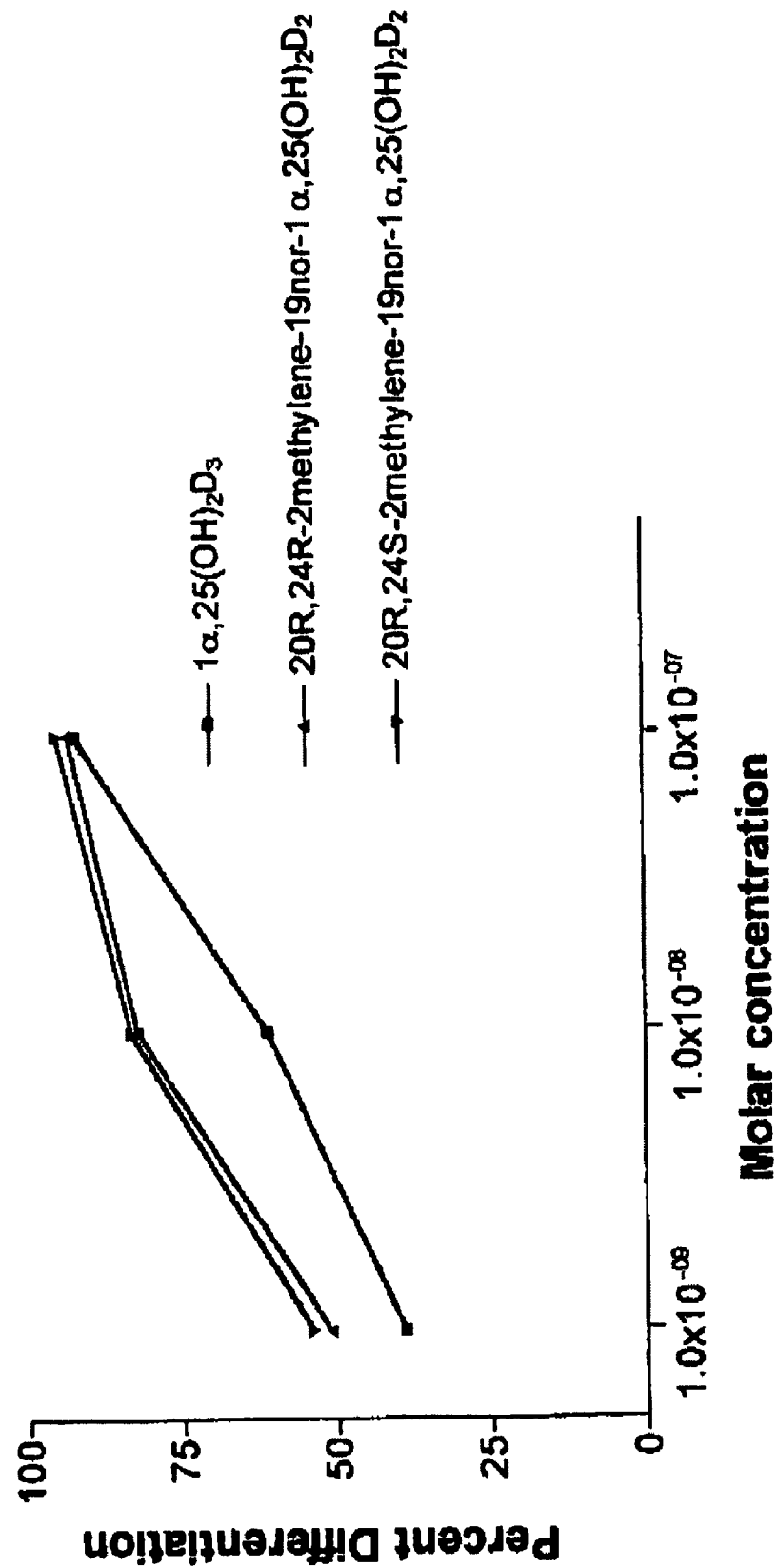
FIG. 2 is a graph illustrating the percent HL-60 cell differentiation as a function of the concentration of 2-methylene-19-nor-24(S)-20(R)-1α,25-dihydroxyvitamin $D_2$, 2-methylene-19-nor-24(R)-20(R)-1α,25-dihydroxyvitamin $D_2$, and 1α,25-dihydroxyvitamin $D_3$.

FIG. 2 illustrates that the 2-methylene-24(S) and 24(R) derivatives of 19-nor-1α,25-dihydroxyvitamin $D_2$ are significantly more potent than 1,25(OH)$_2$D$_3$ on HL-60 differentiation, making them excellent candidates for the treatment of psoriasis and cancer, especially against leukemia, colon cancer, breast cancer and prostate cancer.

Figure 3:
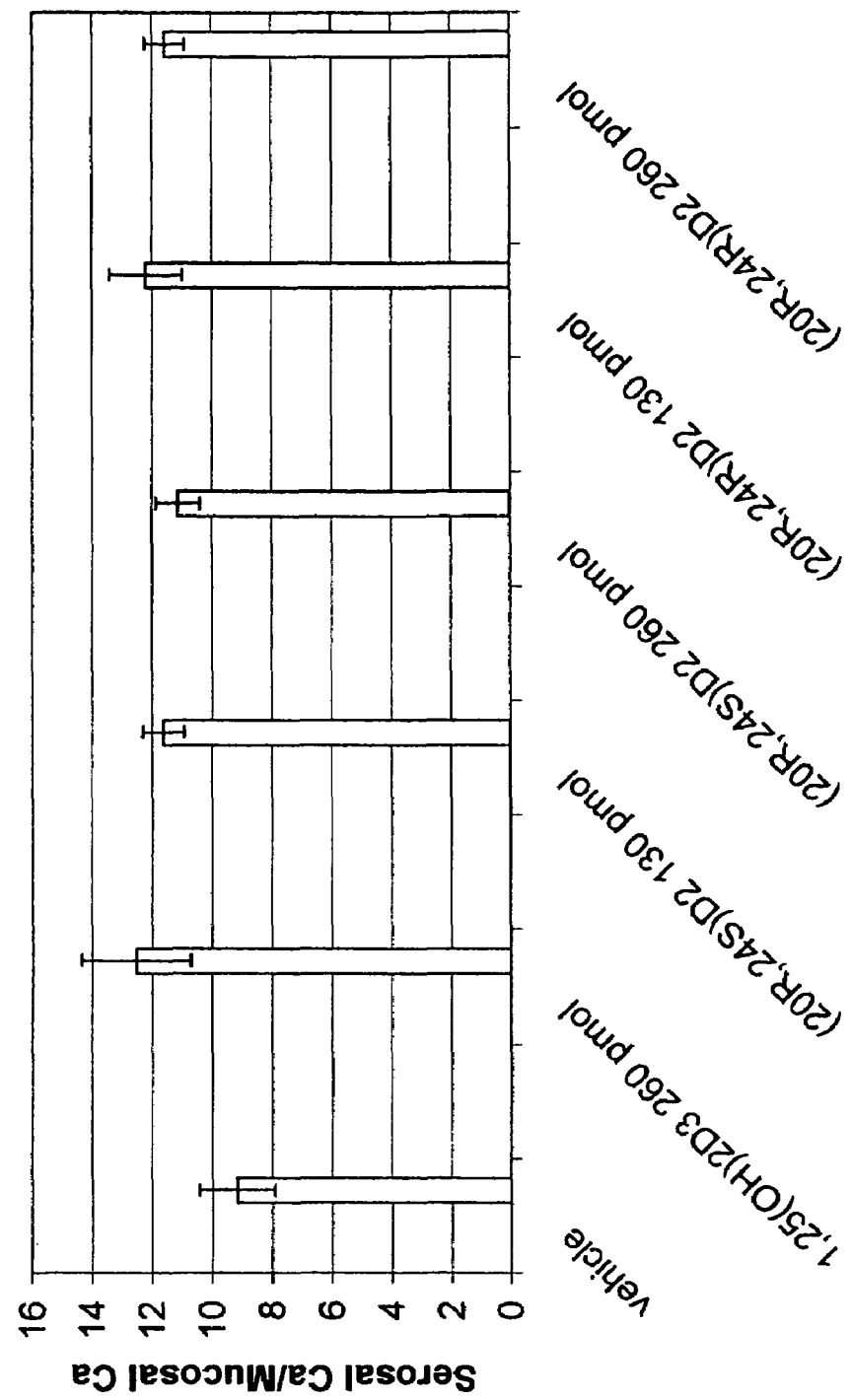
FIG. 3 is a graph illustrating that the 2-methylene-24(S) and 24(R) derivatives of 19-nor-1α,25-dihydroxyvitamin $D_2$ have activity about the same as that of 1α,25-dihydroxyvitamin $D_3$, the natural hormone, in stimulating intestinal calcium transport.

FIG. 3 illustrates that the 2-methylene-24(S) and 24(R) derivatives of 19-nor-1α,25-dihydroxyvitamin $D_2$ have activity about the same as that of 1α,25-dihydroxyvitamin $D_3$, the natural hormone, in stimulating intestinal calcium transport.

Figure 4:
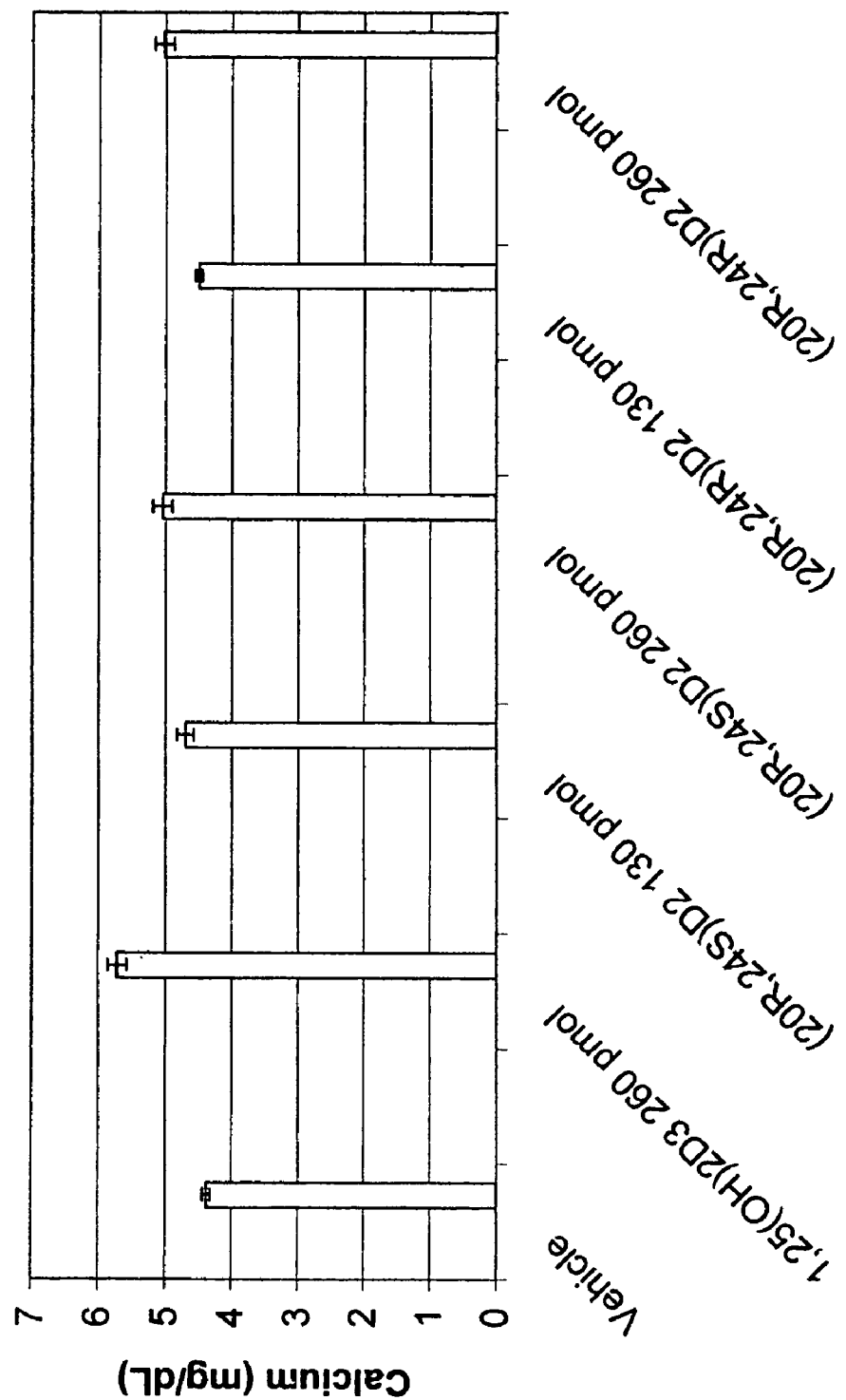
FIG. 4 is a graph illustrating that the 2-methylene-24(S) and 24(R) derivatives of 19-nor-1α,25-dihydroxyvitamin $D_2$ have minimal activity on bone, i.e., the mobilization of calcium from bone, as compared to 1α,25-dihydroxyvitamin $D_3$.

FIG. 4 illustrates that the 2-methylene-24(S) and 24(R) derivatives of 19-nor-1α,25-dihydroxyvitamin $D_2$ have minimal activity on bone, i.e., the mobilization of calcium from bone as compared to 1α,25-dihydroxyvitamin $D_3$.

Competitive binding of the analogs to the porcine intestinal receptor was carried out by the method described by Dame et al. (Biochemistry 25, 4523-4534, 1986).

The differentiation of HL-60 promyelocytic into monocytes was determined as described by Ostrem et al. (J. Biol. Chem. 262, 14164-14171, 1987).

Interpretation of Data

The in vivo tests of serum calcium of rats on a zero calcium diet provides an insight into osteoblastic or bone activity of the 2-methylene-24(S) and 24(R) derivatives of 19-nor-1α,25-dihydroxyvitamin $D_2$. The dose response data in FIG. 4 show that the 2-methylene-24(S) and 24(R) derivatives of 19-nor-1α,25-dihydroxyvitamin $D_2$ have minimal (little, if any) activity as compared to 1,25(OH)$_2$D$_3$ in raising calcium in the plasma via the stimulation of the osteoblasts. At the same time, the activity of the 2-methylene-24(S) and 24(R) derivatives of 19-nor-1α,25-dihydroxyvitamin $D_2$ on intestinal calcium transport is approximately equal to that of 1,25-(OH)$_2$D$_3$ (FIG. 3). Together, these data, therefore, show the 2-methylene-24(S) and 24(R) derivatives of 19-nor-1α,25-dihydroxyvitamin $D_2$ have selective activity on stimulating intestinal calcium transport, but not on bone.

The 2-methylene-24(S) and 24(R) derivatives of 19-nor-1α,25-dihydroxyvitamin $D_2$ are more active than 1,25(OH)$_2$D$_3$ in binding to the vitamin D receptor (FIG. 1), and these compounds are also more active than 1,25-(OH)$_2$D$_3$ in causing differentiation of the promyelocyte, HL-60, into the monocyte (FIG. 2). This result suggests that the 2-methylene-24(S) and 24(R) derivatives of 19-nor-1α,25-dihydroxyvitamin $D_2$ will be very effective in psoriasis because they have direct cellular activity in causing differentiation and in suppressing growth. It also indicates that these compounds will have significant activity as anti-cancer agents, especially against leukemia, colon cancer, breast cancer and prostate cancer.

For treatment purposes, the compounds of this invention defined by formula I, formula IA, and formula IB may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The compound may be administered orally, topically, parenterally, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 μg to 100 μg per day of the compounds are appropriate for treatment purposes, such doses being adjusted according to the disease to be treated, its severity, and the response of the subject as is well understood in the art. Since the compound exhibits specificity of action, each may be suitably administered alone, or together with graded doses of another active vitamin D compound—e.g., 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatment of psoriasis and other malignancies comprise an effective amount of the 2-methylene-24-epi-19-nor-vitamin D compound as defined by the above formula I formula IA, and formula IB as the active ingredient, and a suitable carrier. An effective amount of such compounds for use in accordance with some embodiments of the invention is from about 0.01 μg to about 100 μg per gm of composition, and may be administered topically, transdermally, orally, or parenterally in dosages of from about 0.1 μg/day to about 100 μg/day.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

In some embodiments, the compound is advantageously administered in amounts sufficient to effect the differentiation of promyelocytes to normal macrophages. Dosages, as described above, are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

It is understood that the invention is not limited to the embodiments set forth herein for illustration, but embraces all such forms thereof as come within the scope of the following claims.

What is claimed is:

1. A compound having the formula I, a pharmaceutically acceptable salt of the compound, a mixture comprising the compound or the pharmaceutically acceptable salt of the compound, or a mixture thereof

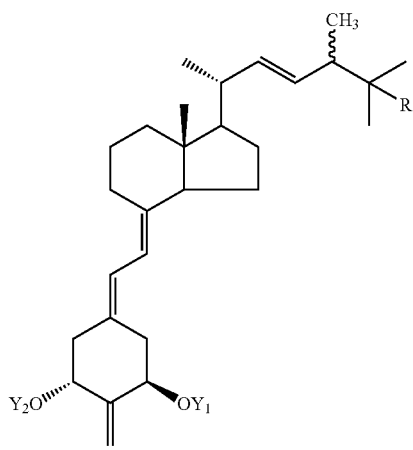

wherein, $Y_1$ and $Y_2$ may be the same or different and are each selected from H, or a hydroxy-protecting group; and R is selected from OH, or a protected hydroxyl group.

2. A pharmaceutical composition comprising a pharmaceutically acceptable excipient and the compound, the pharmaceutically acceptable salt of the compound, the mixture comprising the compound or the pharmaceutically acceptable salt of the compound, or the mixture of claim 1.

3. The compound, the pharmaceutically acceptable salt of the compound, the mixture comprising the compound or the pharmaceutically acceptable salt of the compound, or the mixture of claim 1, wherein the compound has the formula IA

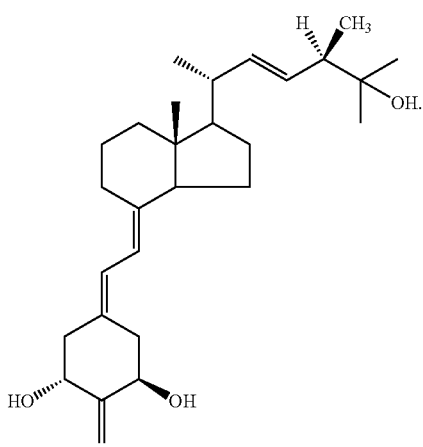

4. A pharmaceutical composition comprising a pharmaceutically acceptable excipient and the compound, the pharmaceutically acceptable salt of the compound, the mixture comprising the compound or the pharmaceutically acceptable salt of the compound, or the mixture of claim 3.

5. The pharmaceutical composition of claim 4, wherein the composition comprises the compound of formula IA in an amount of from about 0.01 μg to about 100 μg per gram of the composition or an equivalent amount of the pharmaceutically acceptable salt of the compound of formula IA.

6. The compound, the pharmaceutically acceptable salt of the compound, the mixture comprising the compound or the pharmaceutically acceptable salt of the compound, or the mixture of claim 1, wherein the compound has the formula IB

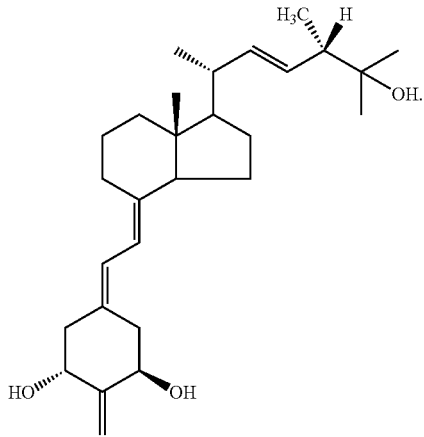

7. A pharmaceutical composition comprising a pharmaceutically acceptable excipient and the compound, the pharmaceutically acceptable salt of the compound, the mixture comprising the compound or the pharmaceutically acceptable salt of the compound, or the mixture of claim 6.

8. The pharmaceutical composition of claim 7, wherein the composition comprises the compound of formula IB in an amount of from about 0.01 μg to about 100 μg per gram of the composition or an equivalent amount of the pharmaceutically acceptable salt of the compound of formula IB.

9. A method of treating a bone disease, comprising administering to a subject having the bone disease an effective amount of the compound, the pharmaceutically acceptable salt of the compound, the mixture comprising the compound or the pharmaceutically acceptable salt of the compound, or the mixture of claim 1 or a pharmaceutical formulation comprising the compound, the pharmaceutically acceptable salt of the compound, the mixture comprising the compound or the pharmaceutically acceptable salt of the compound, or the mixture of claim 1, wherein the bone disease is osteomalacia or osteodystrophy.

10. The method of claim 9, wherein the compound has the formula I.

11. A method of treating a bone disease, comprising administering to a subject having the bone disease an effective amount of the compound, the pharmaceutically acceptable salt of the compound, the mixture comprising the compound or the pharmaceutically acceptable salt of the compound, or the mixture of claim 3 or a pharmaceutical formulation comprising the compound, the pharmaceutically acceptable salt of the compound, the mixture comprising the compound or the pharmaceutically acceptable salt of the compound, or the mixture of claim 3, wherein the bone disease is osteomalacia or osteodystrophy.

12. A method of treating a bone disease, comprising administering to a subject having the bone disease an effective amount of the compound, the pharmaceutically acceptable salt of the compound, the mixture comprising the compound or the pharmaceutically acceptable salt of the compound, or the mixture of claim 6 or a pharmaceutical formulation comprising the compound, the pharmaceutically acceptable salt of the compound, the mixture comprising the compound or the pharmaceutically acceptable salt of the compound, or the mixture of claim 6, wherein the bone disease is osteomalacia or osteodystrophy.

13. The method of claim 9, wherein the compound is administered orally, parenterally, or transdermally.

14. The method of claim 9, wherein the compound is administered in a dosage of from 0.01 μg to 100 μg per day.

15. A method of treating psoriasis, comprising administering to a subject with psoriasis an effective amount of the compound, the pharmaceutically acceptable salt of the compound, the mixture comprising the compound or the pharmaceutically acceptable salt of the compound, or the mixture of claim 1 or a pharmaceutical formulation comprising the compound, the pharmaceutically acceptable salt of the compound, the mixture comprising the compound or the pharmaceutically acceptable salt of the compound, or the mixture of any of claim 1.

16. The method of claim 15, wherein the compound is administered orally, parenterally, transdermally, or topically.

17. The method of claim 15 wherein the compound is administered to the subject in a dosage of from about 0.01 μg/day to about 100 μg/day.

18. A method of treating psoriasis, comprising administering to a subject with psoriasis an effective amount of the compound, the pharmaceutically acceptable salt of the compound, the mixture comprising the compound or the pharmaceutically acceptable salt of the compound, or the mixture of claim 3 or a pharmaceutical formulation comprising the compound, the pharmaceutically acceptable salt of the compound, the mixture comprising the compound or the pharmaceutically acceptable salt of the compound, or the mixture of any of claim 3.

19. A method of treating psoriasis, comprising administering to a subject with psoriasis an effective amount of the compound, the pharmaceutically acceptable salt of the compound, the mixture comprising the compound or the pharmaceutically acceptable salt of the compound, or the mixture of claim 6 or a pharmaceutical formulation comprising the compound, the pharmaceutically acceptable salt of the compound, the mixture comprising the compound or the pharmaceutically acceptable salt of the compound, or the mixture of any of claim 6.

20. A method of treating leukemia, colon cancer, breast cancer, or prostate cancer in a subject comprising administering to the leukemia, colon cancer, breast cancer, or prostate cancer subject an effective amount of the compound, the pharmaceutically acceptable salt of the compound, the mixture comprising the compound or the pharmaceutically acceptable salt of the compound, or the mixture of claim 1 or a pharmaceutical formulation comprising the compound, the pharmaceutically acceptable salt of the compound, the mixture comprising the compound or the pharmaceutically acceptable salt of the compound, or the mixture of claim 1.

21. The method of claim 20, wherein the compound is administered orally, parenterally, or transdermally.

22. The method of claim 20, wherein the compound is administered in a dosage of from about 0.01 μg/day to about 100 μg/day.

23. A method of treating leukemia, colon cancer, breast cancer, or prostate cancer in a subject comprising administering to the leukemia, colon cancer, breast cancer, or prostate cancer subject an effective amount of the compound, the pharmaceutically acceptable salt of the compound, the mixture comprising the compound or the pharmaceutically acceptable salt of the compound, or the mixture of claim 3 or a pharmaceutical formulation comprising the compound, the pharmaceutically acceptable salt of the compound, the mixture comprising the compound or the pharmaceutically acceptable salt of the compound, or the mixture of claim 3.

24. A method of treating leukemia, colon cancer, breast cancer, or prostate cancer in a subject comprising administering to the leukemia, colon cancer, breast cancer, or prostate cancer subject an effective amount of the compound, the pharmaceutically acceptable salt of the compound, the mixture comprising the compound or the pharmaceutically acceptable salt of the compound, or the mixture of claim 6 or a pharmaceutical formulation comprising the compound, the pharmaceutically acceptable salt of the compound, the mixture comprising the compound or the pharmaceutically acceptable salt of the compound, or the mixture of claim 6.

25. A method of treating an autoimmune disease, comprising administering to a patient with the autoimmune disease an effective amount of the compound, the pharmaceutically acceptable salt of the compound, the mixture comprising the compound or the pharmaceutically acceptable salt of the compound, or the mixture of claim 1 or a pharmaceutical formulation comprising the compound, the pharmaceutically acceptable salt of the compound, the mixture comprising the compound or the pharmaceutically acceptable salt of the compound, or the mixture of claim 1.

26. The method of claim 25, wherein the disease is multiple sclerosis.

27. The method of claim 25, wherein the disease is diabetes mellitus.

28. The method of claim 25, wherein the disease is transplant rejection.

29. The method of claim 25, wherein the compound is administered orally, parenterally, or transdermally.

30. The method of claim 25, wherein the compound is administered in a dosage of from about 0.01 μg/day to about 100 μg/day.

31. A method of treating an autoimmune disease, comprising administering to a patient with the autoimmune disease an effective amount of the compound, the pharmaceutically acceptable salt of the compound, the mixture comprising the compound or the pharmaceutically acceptable salt of the compound, or the mixture of claim 3 or a pharmaceutical formulation comprising the compound, the pharmaceutically acceptable salt of the compound, the mixture comprising the compound or the pharmaceutically acceptable salt of the compound, or the mixture of claim 3.

32. A method of treating an autoimmune disease, comprising administering to a patient with the autoimmune disease an effective amount of the compound, the pharmaceutically acceptable salt of the compound, the mixture comprising the compound or the pharmaceutically acceptable salt of the compound, or the mixture of claim 6 or a pharmaceutical formulation comprising the compound, the pharmaceutically acceptable salt of the compound, the mixture comprising the compound or the pharmaceutically acceptable salt of the compound, or the mixture of claim 6.

* * * * *